United States Patent [19]

Reiss

[11] 4,388,409

[45] Jun. 14, 1983

[54] CEMENT TEST DEVICE FOR THE DETECTION OF IMITATION GOLD

[76] Inventor: Andre Reiss, 147-47 Village Rd., Jamaica, N.Y. 11435

[21] Appl. No.: 337,680

[22] Filed: Jan. 7, 1982

[51] Int. Cl.³ .................... G01N 21/78; G01N 33/20
[52] U.S. Cl. .................................. 436/80; 106/89; 422/56; 436/73; 436/169
[58] Field of Search ................ 436/73, 79, 80, 81, 436/82, 83, 84, 169; 422/55, 56; 106/89, 314

[56] References Cited

U.S. PATENT DOCUMENTS

| | | | |
|---|---|---|---|
| 704,409 | 7/1902 | Way | 436/80 |
| 913,129 | 2/1909 | Hames | 436/80 |
| 1,498,073 | 6/1924 | Cohn | 436/84 |
| 2,672,424 | 5/1954 | Avery | 106/89 |
| 3,847,635 | 11/1974 | Lange et al. | 106/89 X |
| 4,054,461 | 10/1977 | Martin | 106/89 |
| 4,160,804 | 7/1979 | Victory | 422/104 |

*Primary Examiner*—Arnold Turk

[57] ABSTRACT

A test device which undergoes a color change when contacted by a metal imitating gold. The device comprises a cast cement carrier impregnated with a complex molybdic acid, a hygroscopic salt, and dilute aqueous acid. A process for making and a method for using the novel test device are disclosed.

7 Claims, No Drawings

CEMENT TEST DEVICE FOR THE DETECTION OF IMITATION GOLD

BACKGROUND OF THE INVENTION

This invention relates to a test device, process for making the test device, and method for using the test device to detect imitation gold.

Imitation gold has traditionally been identified by its solubility in concentrated nitric acid. The liquidity and corrosivity of nitric acid solutions has precluded its use in a pocket portable gold test kit.

It has been mentioned in the literature that free metals in a non-metallic mixture may quickly be identified by contact with aqueous phosphomolybdic acid, the free metal reducing the yellow complex molybdic acid to "molybdenum blue." Reference is directed to Feigl, F., Spot Tests in Inorganic Analysis, Fifth Edition, Elsevier Publishing Co., pp 361-362, 475 (1958). The Inventor has discovered that gold, however, does not reduce the complex molybdic acid.

Therefore, it is an object of this invention to detect imitation gold rather than true gold, by utilizing the color change of a complex molybdic acid in a test composition.

A further object of this invention is to provide a novel solid test device incorporating the test composition to detect imitation gold safely and rapidly.

Another object of this invention is to provide for preparing a safe, solid test device and a method of using this device to rapidly detect imitation gold.

Additional objects of this invention will become evident from the following disclosure.

DISCLOSURE OF THE INVENTION

The invention is embodied in a novel solid test device which undergoes an unequivocal color change when contacted by imitation gold. The test device comprises a cement stone impregnated with an aqueous acidic solution of a complex molybdic acid and a hygroscopic salt.

To prepare the invention, an acidic aqueous solution of the complex molybdic acid and the hygroscopic salt is mixed with a cement carrier, then cast in a suitable mold and allowed to set to stone.

The invention is used by contacting its surface with a metal, the contact area developing a blue color with its intensity being proportional to the non-gold content of the metal. Thus, the invention can detect imitation gold or the purity of gold alloy.

Yellow crystalline phosphomolybdic acid ($20MoO_3.2H_3PO_4.aq$) or silicomolybdic acid ($12MoO_3.H_4SiO_4.aq$) comprise the complex molybdic acid detecting reagents of the invention. Acidification further regulates color intensity, the greater the acidity, the greater the sensitivity of the molybdic acid towards reduction to "molybdenum blue." A pH of 3-5 in the setting composition, preferably attained through use of 0.05 N hydrochloric acid as the aqueous acid, works well though not necessarily limiting for the purpose of the invention.

The hygroscopic salt component of the invention, preferably magnesium chloride or lithium chloride, prevents evaporation of water necessary for reactivity of the molybdic acid.

As the cement carrier component of this invention, dental inlay investment serves well, though not limiting to the invention. Especially convenient is a product named "Cristabolite" (Whip-Mix Corp., Louisville KY 40217), of a pleasing white color and with gold setting properties.

A process for preparing the invention comprises mixing in order the components below, preferably within the ranges in parts by weight:
Dilute aqueous acid: 80-85.
Complex molybdic acid: 5-10.
Hygroscopic salt: 10.
Cement: 150-200.

After the cement has been added and mixed, the composition is cast in a suitable, preferably plastic, mold and allowed to set to stone.

To use the test device of the invention, a metal is placed in contact with the stone surface, the contact area developing an immediate strong blue coloration with imitation gold. Suprisingly, the blue color self-erases in less than thirty minutes allowing constant reuse of the test surface.

The overall structure of the test device is not considered critical, so long as a suitable means is provided for contacting the impregnated stone surface with the metal to be tested.

The invention will be further disclosed in the examples below, which are intended to be illustrative and not to be construed as limitations on the scope of the invention.

EXAMPLE 1

A solution was prepared by combining in an all glass mixing vessel with continuous stirring, the following compounds in the order listed:
0.05 N Hydrochloric acid: 50 g.
Phosphomolybdic acid: 4 g.
Magnesium Chloride: 5 g.
Cristabolite: 100 g.
Thirty seconds after addition of the Cristabolite, the composition was poured in a plastic box and allowed to set for an hour. Contact of imitation gold, in this case a highly polished brass ring, to the yellow stone surface caused an immediate dark blue coloration at the point of contact. 14 karat gold contacted to the stone surface colored the stone a very pale blue. Contact of pure gold to the stone colored it not at all.

EXAMPLE 2

A composition was prepared as described in example (1) except that 0.10 N Hydrochloric acid was substituted. The brass ring colored the stone on contact a little darker, 14 k gold about twice as dark blue, pure gold not at all.

EXAMPLE 3

A composition was prepared as described in example (1) except that 4 g Silicomolybdic acid and 5 g Lithium Chloride were substituted for the Phosphomolybdic acid and Magnesium Chloride respectively. This composition was observed to have the same essential properties as in example (1).

I claim:

1. A test device for the detection of imitation gold or the purity of gold alloy comprising a cast cement carrier impregnated with an aqueous acidic solution of a complex molybdic acid and a hygroscopic salt.

2. The device of claim 1 wherein the cement carrier comprises a white dental inlay investment.

3. The device of claim 1 wherein the complex molybdic acid comprises phosphomolybdic acid or silicomolybdic acid.

4. The device of claim 1 wherein the acidic component comprises dilute aqueous hydrochloric acid.

5. The device of claim 1 wherein the hygroscopic salt comprises magnesium chloride or lithium chloride.

6. A process for preparing the device of claim 1 comprising mixing aqueous acid, complex molybdic acid, hygroscopic salt, and cement; then casting the composition in a mold.

7. A method for the detection of imitation gold or the purity of gold alloy comprising contacting the cast cement carrier of claim 1 with a metal; and observing the contact area on the cement carrier for the intensity of a blue color.

* * * * *